United States Patent [19]

Sacks

[11] 4,442,035
[45] Apr. 10, 1984

[54] ACYCLIC AMINE EPOXIDE PROCESS

[75] Inventor: Clifford E. Sacks, Portage, Mich.

[73] Assignee: The Upjohn Company, Kalamazoo, Mich.

[21] Appl. No.: 436,219

[22] Filed: Oct. 25, 1982

Related U.S. Application Data

[63] Continuation-in-part of Ser. No. 431,548, Sep. 30, 1982, abandoned.

[51] Int. Cl.$^3$ .............................................. C07J 71/00
[52] U.S. Cl. ...................... 260/239.55 R; 260/397.45
[58] Field of Search ....................... 260/397.45, 239.55

[56] References Cited

U.S. PATENT DOCUMENTS

| | | | |
|---|---|---|---|
| 2,838,493 | 6/1958 | Graber et al. | 260/239.55 |
| 3,255,185 | 6/1966 | Murrill | 260/239.55 |
| 3,499,016 | 3/1970 | Lincoln et al. | 260/397.45 |
| 3,725,392 | 4/1973 | Beal et al. | 260/239.55 |
| 3,980,778 | 9/1976 | Ayer | 424/243 |
| 4,207,235 | 6/1980 | Howarth et al. | 260/239.55 |

OTHER PUBLICATIONS

H. Oediger et al., Bicyclic Amidines as Reagents in Org. Syntheses, Synthesis 591 (1972).

D. M. R. Barton et al., Synthesis and Properties of a Series of Strong But Hindered Organic Bases, J.C.S. Chem. Comm. 1136 (1981).

J. A. Hogg et al., Adrenal Hormones, etc., J. Am. Chem. Soc. 77, 4438 (1955).

*Primary Examiner*—Elbert L. Roberts
*Attorney, Agent, or Firm*—Bruce Stein

[57] ABSTRACT

Acyclic amines are used to transform 9α-substituted-11β-hydroxy 21-acyloxy steroids to the corresponding 9β,11β-epoxy 21-acyloxy steroids without removal of the $C_{17}$ or $C_{21}$ ester. The acyclic amines are cheaper and easier to prepare than previously disclosed dehydrohalogenating agents which do not produce cleavage of the $C_{21}$ ester.

33 Claims, No Drawings

4,442,035

ACYCLIC AMINE EPOXIDE PROCESS

CROSS REFERENCE TO RELATED APPLICATION

This patent application is a continuation-in-part patent application of co-pending patent application Ser. No. 431,548, filed Sept. 30, 1982 and now abandoned.

BACKGROUND OF THE INVENTION

The transformations of $\Delta^{9(11)}$-steroids to the corresponding bromohydrins ($9\alpha$-bromo-$11\beta$-hydroxy steroid) then to the corresponding $9\beta,11\beta$-epoxy steroids and finally by reaction with hydrogen fluoride to the desired $9\alpha$-fluoro-$11\beta$-hydroxy steroids are well known. Various agents have been used for the epoxidation reaction including strong bases such as methoxide, t-butoxide or sodium hydroxide in methanol (U.S. Pat. Nos. 2,838,493 and 3,725,392), potassium acetate in acetone (U.S. Pat. No. 3,980,778), and J. Am. Chem. Soc. 77, 4438 (1955), potassium fluoride in particular solvents (U.S. Pat. No. 3,255,185) and cyclic amidine bases such as DBU (U.S. Pat. No. 4,207,235).

The closure of the $9\alpha$-bromo-$11\beta$-hydroxy bromohydrin to the corresponding $9\beta,11\beta$-epoxide is a dehydrohalogenation reaction.

H. Oediger, et al. in Synthesis 591 (1972) compare the elimination of hydrogen chloride by various organic bases. Table 1 on p. 592 shows that cyclic and acyclic amines and acyclic amidines do not work in the dehydrohalogenation reaction nearly as well as DBN. Hence, it would be expected that acyclic amidines would not transform the $9\alpha$-bromo-$11\beta$-hydroxy bromohydrin to the corresponding $9\beta,11\beta$-epoxide nearly as well as does DBN or DBU.

D. H. R. Barton in J.C.S. Chem. Comm. 1136 (1981) reports the preparation of a number of guanidines which are strong organic bases. Barton did not report that these bases would be useful in a dehydrohalogenation reaction such as the transformation of a bromohydrin to the corresponding epoxide.

The present invention involves acyclic guanidines and amidines which surprisingly and unexpectedly efficiently effect the transformation of $9\alpha$-substituted-$11\beta$-hydroxy steroids (I) to the corresponding $9\beta,11\beta$-epoxides (II). The guanidines (III) and amidines (IV) are less expensive and easier to make than other known dehydrohalogenating agents such as DBU and DBN and do not cleave 21-acyloxy groups as to most other bases.

BRIEF DESCRIPTION OF THE INVENTION

Disclosed is a process for the preparation of an epoxide of formula (II) which comprises contacting a $9\alpha$-substituted-$11\beta$-hydroxy steroid of formula (I) with an acyclic amine selected from the group consisting of guanidines of formula (III) and amidines of the formula (IV) and isolating the epoxide (II).

DETAILED DESCRIPTION OF THE INVENTION

The $9\alpha$-substituted-$11\beta$-hydroxy steroid (I) starting materials are well known to those skilled in the art or can be readily prepared by known methods from compounds well known to those skilled in the art.

The process of the present invention for the transformation of the $9\alpha$-substituted-$11\beta$-hydroxy steroid (I) to the epoxide (II) is operable with a wide widely of steroid A-rings. Preferred are the $\Delta^4$-3-keto (A), $\Delta^{1,4}$-3-keto (B) and $3\beta$-hydroxy-$\Delta^5$ (C) steroid A rings, see Chart B.

The fluorine atom or methyl group at the C-6 position does not interfere in any way in the process of the present invention. The leaving group, $R_9$, is a chlorine, bromine or iodine atom or a hydroxyl group as the tosylate, mesylate or triflate ester. It is preferred that $R_9$ be a bromine atom. $R_{16}$ is a hydrogen atom, hydroxyl or methyl group. When $R_{16}$ is a hydroxyl group and there is a hydroxyl group at $C_{17}$, the hydroxyl groups can be in the form of an acetonide. $R_{17}$ is a hydrogen atom or $-COR_{17}\alpha$ wherein $R_{17}\alpha$ is alkyl of one thru 6 carbon atoms or phenyl. When $R_{17}$ is a hydrogen atom and $R_{16}$ is a hydroxyl group, the hydroxyl groups can be in the form of an acetonide. $R_{21}$ is alkyl of one thru 6 carbon atoms, phenyl or phenyl substituted with p-nitro or m-methoxy groups. The process of the present invention is applicable equally to $\Delta^4$-3-keto steroids and $\Delta^{1,4}$-3-keto steroids. The preferred steroid D ring is that set forth in Chart C as formula (D).

The acyclic amidines (IV) are known to those skilled in the art or can be readily prepared from known compounds by methods well known to those skilled in the art, see, for example, J. Am. Chem. Soc. 102, 7125 (1980) and M. Bredereck et al., Chem. Ber, 96, 1350 (1963). $R_a$ is alkyl of one thru 7 carbon atoms, cycloalkyl of 5 thru 7 carbon atoms or phenyl substituted with one thru 3 $-R$, $-OR_{50}$ or $-N(R_{50})_2$ where with the amine the $R_{50}$'s can be the same or different and can be combined to form a secondary amine selected from the group consisting of piperidine, pyrrolidine or morpholine. It is preferred that $R_a$ be t-butyl. $R'_3$ and $R'_4$ can be the same or different and are alkyl of one thru 7 carbon atoms, cycloalkyl of 5 thru 7 carbon atoms or phenyl substituted with one thru 3 $-R$, $-OR_{50}$ or $-N(R_{50})_2$ with the proviso that $R'_3$ and $R'_4$ combined cannot have more than 14 carbon atoms; $R'_3$ and $R'_4$ can be combined to form a cyclic secondary amine selected from the group consisting of piperidine, pyrrolidine and morpholine. It is preferred that both $R'_3$ and $R'_4$ be methyl.

The guanidines of formula (III) are well known to those skilled in the art or can be readily prepared from known compounds by methods well known by those skilled in the art. See Barton, supra. $R_g$ is identical with $R_a$ except that it also includes the hydrogen atom, phenyl and p-tolyl group. It is preferred that $R_g$ be a hydrogen atom. $R_1$, $R_2$, $R_3$ and $R_4$ are the same or different and are alkyl of one thru 7 carbon atoms, cycloalkyl of 5 thru 7 carbon atoms, phenyl substituted with zero thru 3, $-R$, $-OR_{50}$ or $-N(R_{50})_2$ where with the amine the $R_{50}$'s can be the same or different and can be combined to form a secondary amine selected from the group consisting of piperidine, pyrrolidine or morpholine with the proviso that $R_1$-$R_2$ and $R_3$-$R_4$ combined cannot have more than 14 carbon atoms; $R_1$-$R_2$ and $R_3$-$R_4$ can be combined to form a cyclic secondary amine selected from the group consisting of piperidine, pyrrolidine and morpholine. It is preferred that $R_1$, $R_2$, $R_3$ and $R_4$ a 11 be methyl groups or hydrogen atoms.

Tables 1 and 2 disclose that while the guanidines (III) and amidines (IV) are operable in the process of the present invention some are preferred.

The $9\alpha$-substituted-$11\beta$-hydroxy steroid (I) is contacted with either an acyclic guanidine (III) or an acyclic amidine (IV) in an aprotic polar organic solvent selected from the group consisting of methylene chloride, acetone, ethyl acetate, DMSO, DMF, THF, dioxane, acetonitrile, toluene and chloroform. It is preferred that the aprotic polar solvent be DMF.

One to two equivalents of the guanidine (III) or amidine (IV) per equivalent of steroid are used. It is preferred that approximately 1.1 equivalents of the guanidine (III) or amidine (IV) per equivalent of steroid be used.

The reaction is preferably performed under a nitrogen atmosphere although this is not necessary.

The reaction is performed in the temperature range of 0°–100° depending on the nature of the guanidine (III) or amidine (IV) used. When the acyclic amine is the guanidine (III) the reaction is generally performed in the temperature range of 0°–40° with 25°–35° being preferred. When the acyclic amine is the amidine (IV) the reaction is generally performed in the temperature range of 70°–100° with 80°–90° being preferred. The reaction can be performed in a sealed container with heat which shortens the reaction time. Generally the reaction is performed at the reflux temperature of the organic diluent being used.

The reaction is monitored by TLC which generally indicates the reaction is complete in approximately one hr with guanidines (III) and approximately 4–5 hr with the amidines (IV).

When the reaction is complete as measured by TLC the reaction mixture is diluted with water containing an acid such as hydrochloric, acetic, sulfuric, phosphoric, or p-TSA. The desired epoxide (II) is extracted from the reaction medium by methods well known to those skilled in the art or isolated by water knock-out and filtration.

The epoxides (II) are useful for conversion to the corresponding 9α-fluoro-11β-hydroxy steroids by reaction of the epoxide with hydrogen fluoride as is well known to those skilled in the art, see Fried, et al., J. Am. Chem. Soc. 76,1455 (1954); Hirschman, et al., J. Am. Chem. Soc. 4957 (1956); U.S. Pat. Nos. 2,894,007, 3,049,556, 3,086,032, 3,007,923, 3,211,758 and 3,980,778.

Therefore the process of the present invention permits transformation of the 9α-substituted-11β-hydroxy 21-esters to the corresponding 9β,11β-epoxide 21-esters (II) without cleavage of the 21 ester group utilizing bases which are less expensive and more easily prepared than DBU and DBN.

DEFINITIONS

The definitions and explanations below are for the terms as used throughout the entire patent application including both the specification and the claims.

All temperatures are in degrees Centigrade.
TLC refers to thin-layer chromatography.
THF refers to tetrahydrofuran.
DMSO refers to dimethylsulfoxide.
DMF refers to dimethylformamide.
p-TSA refers to p-toluenesulfonic acid, monohydrate.
When solvent pairs are used, the ratio of solvents used are volume/volume (v/v).
DBU refers to 1,8-diazabicyclo[5.4.0]undec-7-ene.
DBN refers to 1,5-diazabicyclo[4.3.0]non-5-ene.
When the term of "___thru___carbon atoms" is used, it includes isomers thereof.
R is alkyl of 1 thru 3 carbon atoms.
$R_a$ is alkyl of one thru 7 carbon atoms, cycloalkyl of 5 thru 7 carbon atoms, phenyl substituted with one thru 3—R, —$OR_{50}$ or —$N(R_{50})_2$ where with the amine the $R_{50}$'s can be the same or different and can be combined to form a cyclic secondary amine selected from the group consisting of piperidine, pyrrolidine and morpholine.

$R_g$ is $R_a$ and a hydrogen atom, or phenyl.

$R_1$ is alkyl of one thru 7 carbon atoms, cycloalkyl of 5 thru 7 carbon atoms, phenyl substituted with zero thru 3—R, —$OR_{50}$ or —$N(R_{50})_2$ where with the amine the $R_{50}$'s can be the same or different and can be combined to form a cyclic secondary amine selected from the group consisting of piperidine, pyrrolidine and morpholine with the proviso that $R_1$ and $R_2$ combined cannot have more than 14 carbon atoms; $R_1$ and $R_2$ can be combined to form a cyclic secondary amine selected from the group consisting of piperidine, pyrrolidine and morpholine.

$R_2$ is alkyl of one thru 7 carbon atoms, cycloalkyl of 5 thru 7 carbon atoms, phenyl substituted with zero thru 3—R, —$OR_{50}$ or —$N(R_{50})_2$ where with the amine the $R_{50}$'s can be the same or different and can be combined to form a cyclic secondary amine selected from the group consisting of piperidine, pyrrolidine and morpholine with the proviso that $R_1$ and $R_2$ combined cannot have more than 14 carbon atoms; $R_1$ and $R_2$ can be combined to form a cyclic secondary amine selected from the group consisting of piperidine, pyrrolidine and morpholine.

$R_3$ is alkyl of one thru 7 carbon atoms, cycloalkyl of 5 thru 7 carbon atoms, phenyl substituted with zero thru 3—R, —$OR_{50}$ or —$N(R_{50})_2$ where with the amine the $R_{50}$'s can be the same or different and can be combined to form a cyclic secondary amine selected from the group consisting of piperidine, pyrrolidine and morpholine with the proviso that $R_3$ and $R_4$ combined cannot have more than 14 carbon atoms; $R_3$ and $R_4$ can be combined to form a cyclic secondary amine selected from the group consisting of piperidine, pyrrolidine and morpholine.

$R_3'$ is alkyl of one thru 7 carbon atoms, cycloalkyl of 5 thru 7 carbon atoms, phenyl substituted with one thru 3—R, —$OR_{50}$ or —$N(R_{50})_2$ where with the amine the $R_{50}$'s can be the same or different and can be combined to form a secondary amine selected from the group consisting of piperidine, pyrrolidine or morpholine, with the proviso that $R_3'$ and $R_4'$ combined cannot have more than 14 carbon atoms; $R_3'$ and $R_4'$ combined cannot have more than 14 carbon atoms; $R_3'$ and $R_4'$ can be combined to form a cyclic secondary amine selected from the group consisting of piperidine, pyrrolidine and morpholine.

$R_4$ is alkyl of one thru 7 carbon atoms, cycloalkyl of 5 thru 7 carbon atoms, phenyl substituted with zero thru 3—R, —$OR_{50}$ or —$N(R_{50})_2$ where with the amine the $R_{50}$'s can be the same or different and can be combined to form a cyclic secondary amine selected from the group consisting of piperidine, pyrrolidine and morpholine with the proviso that $R_3$ and $R_4$ combined cannot have more than 14 carbon atoms; $R_3$ and $R_4$ can be combined to form a cyclic secondary amine selected from the group consisting of piperidine, pyrrolidine and morpholine.

$R_4'$ is alkyl of one thru 7 carbon atoms, cycloalkyl of 5 thru 7 carbon atoms, phenyl substituted with one thru 3—R, —$OR_{50}$ or —$N(R_{50})_2$ where with the amine the $R_{50}$'s can be the same or different and can be combined to form a secondary amine selected from the group consisting of piperidine, pyrrolidine or morpholine, with the proviso that $R_3'$ and $R_4'$ combined cannot have more than 14 carbon atoms; $R_3'$ and $R_4'$ can be combined to form a cyclic secondary amine selected from the group consisting of piperidine, pyrrolidine and morpholine.

$R_6$ is a hydrogen or fluorine atom or methyl group.

$R_9$ is a chlorine, bromine or iodine atom or hydroxyl group as the tosylate, mesylate, or triflate ester.

$R_{16}$ is a hydrogen atom, hydroxyl, acyloxy where the acyl group contains 2 thru 6 carbon atoms, or methyl group with the proviso that when $R_{16}$ is a hydroxyl group and when $R_{17}$ is a hydrogen atom the hydroxyl groups at $C_{16}$ and $C_{17}$ can be in the form of an acetonide.

$R_{17}$ is a hydrogen atom or a —$COR_{17\alpha}$ group with the proviso that when $R_{17}$ is a hydrogen atom and $R_{16}$ is a hydroxyl group the hydroxyl groups at $C_{16}$ and $C_{17}$ can be in the form of an acetonide.

$R_{17\alpha}$ is an alkyl of one thru 6 carbon atoms or phenyl.

$R_{21}$ is alkyl of one thru 6 carbon atoms or phenyl, or phenyl substituted with p-nitro or m-methoxy groups.

$R_{50}$ is a hydrogen atom or alkyl of 1 thru 3 carbon atoms.

~ indicates the attached atom or group can be in the alpha or beta configuration.

...... is a single or double bond.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

9$\beta$,11$\beta$-Epoxy-17$\alpha$,21-dihydroxypregna-1,4-diene-3,20-dione 21-acetate (II)

9$\alpha$-Bromo-11$\beta$,17$\alpha$,21-trihydroxypregna-1,4-diene-3,20-dione 21-acetate (I, JACS 77, 4438 (1955), 2.406 g) in DMF (12 ml) is stirred under nitrogen in a 12° water bath. Tetramethylguanidine (0.656 ml) is added to the mixture which is stirred overnight. Water (20 ml) containing hydrochloric acid (1 N, 1.0 ml) is added with stirring. The mixture is cooled in an ice water bath during the water/hydrochloric acid addition. Water (13 ml) is slowly added to the mixture at −10° with stirring. The mixture is stirred at 6° for 20 min. The solid is filtered, washed three times with water and dried under reduced pressure at 50°–60° for 3½ hr to give the title compound.

EXAMPLE 2

9$\beta$,11$\beta$-Epoxy-17$\alpha$,21-dihydroxypregn-4-ene-3,20-dione 21-acetate (II)

9$\alpha$-Bromo-11$\beta$,17$\alpha$,21-trihydroxypregn-4-ene-3,20-dione 21-acetate (I, JACS 77, 4438 (1955), 2.00 g) is dissolved in DMF (5 ml). Tetramethylguanidine (0.475 g) is added and the mixture is stirred at 20°–25°. When TLC indicated the reaction is done, water containing 10% hydrochloric acid is added, the mixture stirred, the solids are collected by filtration, washed, and dried under reduced pressure to give the title compound.

EXAMPLE 3

9$\beta$,11$\beta$-Epoxy-17$\alpha$,21-dihydroxy-16$\beta$-methylpregna-1,4-diene-3,20-dione 21-benzoate (II)

9$\alpha$-Bromo-11$\beta$,17$\alpha$,21-trihydroxy-16$\beta$-methylpregna-1,4-diene-3,20-dione 21-benzoate (I, U.S. Pat. No. 3,164,618, Example 30, 2.0 g) is slurried in methylene chloride (10 ml). t-Butyldimethylamidine (0.86 g) is added and the mixture heated to reflux. After 6 hr TLC indicates the reaction is about 90% complete. The organic solvent is replaced with ethyl acetate, the mixture filtered and the solid dried under reduced pressure to give the title compound.

EXAMPLE 4

9$\beta$,11$\beta$-Epoxy-17$\alpha$,21-dihydroxy-16$\alpha$-methylpregna-1,4-diene-3,20-dione 21-acetate (II)

9$\alpha$-Bromo-11$\beta$,17$\alpha$,21-trihydroxy-16$\alpha$-methylpregna-1,4,-diene-3,20-dione 21-acetate (I, U.S. Pat. No. 3,164,618, Example 40(c), 1.00 g) is slurried in methylene chloride (5 ml). t-Butyldimethylamidine (0.43 ml) is added and the mixture heated to reflux overnight. The methylene chloride is replaced with ethyl acetate, the mixture filtered, and the solids dried under reduced pressure to give the title compound.

EXAMPLE 5

Comparison of Expoxidation Reaction using DBU and Tetramethylguanidine

A. DBU

9$\alpha$-Bromo-11$\beta$,17$\alpha$,21-trihydroxypregn-4-ene-3,20-dione 21-acetate (I, 4.0 g) and DMF (20 ml) were mixed at 5°. DBU (1.49 ml, 9.94 mmole) was added. After 15 min, water (50 ml) containing 10% aqueous hydrochloric acid was added, the mixture was stirred and filtered, the solids were washed with water and dried to give 9$\beta$,11$\beta$-epoxy-17$\alpha$,21-dihydroxy-pregna-4-ene-3,20-dione 21-acetate (II) in 93.2% yield.

B. Tetramethylguanidine

9$\alpha$-Bromo-11$\beta$,17$\alpha$,21-trihydroxypregn-4-ene-3,20-dione 21-acetate (I, 4.0 g) and DMF (20 ml) were mixed at 5°. Tetramethylguanidine (1.24 ml, 9.94 mmole) was added. After 15 min, water (50 ml) containing 10% aqueous hydrochloric acid was added. The mixture was stirred and filtered. The solids were washed with water and dried to give 9$\beta$,11$\beta$-epoxy-17$\alpha$,21-dihydroxy-pregn-4-ene-3,20-dione 21-acetate (II) in 92.3% chemical yield.

EXAMPLE 6

6$\alpha$-Fluoro-9$\beta$,11$\beta$-epoxy-16$\alpha$,17$\alpha$,21-trihydroxypregna-1,4-diene-3,20-dione 16,17-acetonide-21-acetate (II)

9$\alpha$-Bromo-6$\alpha$-fluoro-11$\beta$,16$\alpha$,17$\alpha$,21-tetrahydroxypregna-1,4-diene-3,20-dione 16,17-acetonide-21-acetate (I, J. Am. Chem. Soc. 77, 4438 (1957), 2.64 g) is dissolved in DMF (15 ml) at 20°–25°. Tetramethylguanidine (III, 0.62 g) is added, and the mixture stirred for 15 min. Water (30 ml) and a little hydrochloric acid (10%) are added. The mixture is cooled and filtered. The solids are washed with cold water and dried in an oven overnight to give the title compound.

EXAMPLE 7

9β,11β-Epoxy-16α,17α,21-trihydroxypregn-4-ene-3,20-dione 16,21-diacetate (II)

Following the general procedure of Example 1 and making non-critical variations, but starting with 9α-bromo-11β,16α,17α,21-tetrahydroxypregn-4-ene-3,20-dione 16,21-diacetate (I, J. Am.Chem. Soc. 81, 1689 (1959)), the title compound is obtained.

EXAMPLE 8

9β,11β-Epoxy-16α,17α,21-trihydroxypregna-1,4-diene-3,20-dione 16,21-diacetate (II)

Following the general procedure of Example 1 and making non-critical variations, but starting with 9α-bromo-11β,16α,17α,21-tetrahydroxypregna-1,4-diene-3,20-dione 16,21-diacetate (I, J. Am. Chem. Soc. 81, 1686 (1959)), the title compound is obtained.

EXAMPLE 9

9β,11β-Epoxy-17α,21-dihydroxypregn-4-ene-3,20-dione 21-acetate (II)

Following the general procedure of Example 5B and making non-critical variations but using guanidine in place of tetramethylguanidine, the title compound is obtained.

EXAMPLES 10–20

Following the procedure of Example 1 and making non-critical variations but starting with the 9α-substituted-11β-hydroxy steroid (I) of Column A, the epoxide (II) of Column B is obtained.

| Example | Column A | Column B |
|---|---|---|
| 10 | 9α-Bromo-11β,16α,17α,21-tetrahydroxypregn-4-en-3,20-dione 21-acetate | 9β,11β-Epoxy-16α,17α,21-trihydroxypregn-4-en-3,20-dione 21-acetate |
| 11 | 6α-Fluoro-9α-bromo-11β,16α,17α,21-tetrahydroxypregn-4-en-3,20-dione 21-acetate | 9β,11β-Epoxy-6α-fluoro-16α,17α,21-trihydroxypregn-4-en-3,20-dione 21-acetate |
| 12 | 9α-Bromo-11β,16α,17α,21-tetrahydroxypregna-1,4-diene-3,20-dione 21-acetate | 9β,11β-Epoxy-16α,17α,21-trihydroxypregna-1,4-diene-3,20-dione 21-acetate |
| 13 | 6α-Fluoro-9α-bromo-11β-16α,17α,21-tetrahydroxy-pregna-1,4-diene-3,20-dione 21-acetate | 9β,11β-Epoxy-6α-fluoro-16α,17α,21-trihydroxy-pregna-1,4-diene-3,20-dione 21-acetate |
| 14 | 9α-Bromo-11β,17α,21-trihydroxy-16β-methylpregna-1,4-diene-3,20-dione 17,21-diacetate | 9β,11β-Epoxy-17α,21-dihydroxy-16β-methylpregna-1,4-diene-3,20-dione 17,21-diacetate |
| 15 | 9α-Bromo-11β,17α,21-trihydroxy-16β-methylpregna-1,4-diene-3,20-dione 17-benzoate | 9β,11β-Epoxy-17α,21-dihydroxy-16β-methylpregna-1,4-diene-3,20-dione 17-benzoate |
| 16 | 9α-Bromo-11β,17α,21-trihydroxy-16β-methylpregna-1,4-diene-3,20-dione 21-pivalate | 9β,11β-Epoxy-17α,21-dihydroxy-16β-methylpregna-1,4-diene-3,20-dione 21-pivalate |
| 17 | 9α-Bromo-11β,17α,21-trihydroxy-16β-methylpregna 1,4-diene-3,20-dione 21-valerate | 9β,11β-Epoxy-17α,21-dihydroxy-16β-methylpregna-1,4-diene-3,20-dione 21-valerate |
| 18 | 9α-Bromo-11β,17α,21-trihydroxy-16β-methylpregna-1,4-diene-3,20-dione 21-propionate | 9β,11β-Epoxy-17α,21-dihydroxy-16β-methylpregna-1,4-diene-3,20-dione 21-propionate |
| 19 | 9α-Bromo-11β,17α,21-trihydroxy-16β-methylpregna-1,4-diene-3,20-dione 17,21-dipropionate | 9β,11β-Epoxy-17α,21-dihydroxy-16β-methylpregna-1,4-diene-3,20-dione 17,21-dipropionate |
| 20 | 6α-Fluoro-9α-bromo-11β,17α,21-trihydroxy-pregna-1,4-diene-3,20-dione 17,21-diacetate | 9β,11β-Epoxy-6α-fluoro-17α,21-dihydroxy-pregna-1,4-diene-3,20-dione 17,21-diacetate |

TABLE 1

| | | Guanidine Bases | | | |
|---|---|---|---|---|---|
| $R_g$ | $R_1$ | $R_2$ | $R_3$ | $R_4$ | Score |
| hydrogen | hydrogen | hydrogen | hydrogen | hydrogen | ++++ |
| hydrogen | methyl | methyl | methyl | methyl | ++++ |
| p-tolyl | morpholine | | hydrogen | p-tolyl | +++ |
| i-propyl | phenyl | phenyl | hydrogen | i-propyl | +++ |
| p-tolyl | pyrrolidine | | hydrogen | p-toly | ++ |
| i-propyl | cyclohexyl | cyclohexyl | hydrogen | i-propyl | ++ |
| i-propyl | pyrrolidine | | hydrogen | i-propyl | + |
| cyclohexyl | methyl | methyl | hydrogen | cyclohexyl | + |

TABLE 2

| | Amidine Bases | | |
|---|---|---|---|
| $R_9$ | $R_3$ | $R_4$ | Score |
| t-butyl | methyl | methyl | ++ |
| n-butyl | methyl | methyl | + |
| cyclohexyl | methyl | methyl | + |
| phenyl | methyl | methyl | − |

CHART A

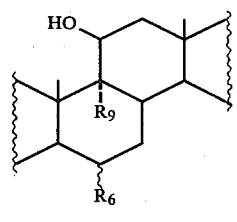

(I)

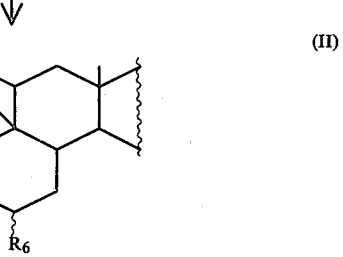

(II)

CHART B

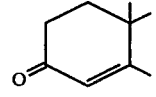

(A)

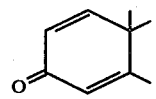

(B)

-continued
CHART B

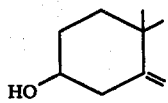
(C)

CHART C

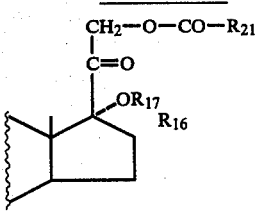
(D)

$$R_g-N=C(R_3)-N(R_4)-N(R_2)-R_1 \quad (III)$$

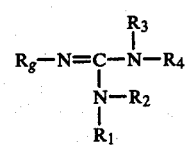

$$R_a-N=CH-N(R_3')-R_4' \quad (IV)$$

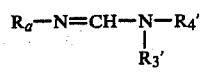

I claim:

1. A process for the preparation of an epoxide of the formula

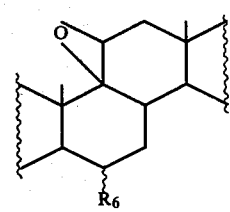
(II)

which comprises (1) contacting a 9α-substituted 11β-hydroxy steroid of the formula

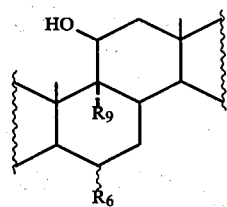
(I)

with an acyclic amine selected from the group consisting of compounds of the formula

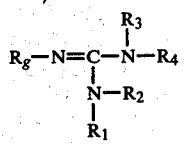
(III)

-continued

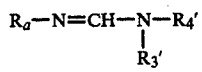
(IV)

and (2) isolating the epoxide (II) where $R_a$ is alkyl of one through 7 carbon atoms, cycloalkyl of 5 through 7 carbon atoms, phenyl substituted with one through 3—R, —$OR_{50}$ or —$N(T_{50})_2$ where with the amine the $R_{50}$'s can be the same or different and can be combined to form a cyclic secondary amine selected from the group consisting of piperidine, pyrrolidine and morpholine;

$R_g$ is $R_a$ and a hydrogen atom, or phenyl;

$R_1$ is alkyl of one through 7 carbon atoms, cycloalkyl of 5 through 7 carbon atoms, phenyl substituted with zero through 3—R, —$OR_{50}$ or —$N(R_{50})_2$ where with the amine the $R_{50}$'s can be the same or different and can be combined to form a cyclic secondary amine selected from the group consisting of piperidine, pyrrolidine and morpholine with the proviso that $R_1$ and $R_2$ combined cannot have more than 14 carbon atoms; $R_1$ and $R_2$ can be combined to form a cyclic secondary amine selected from the group consisting of piperidine, pyrrolidine and morpholine;

$R_2$ is alkyl of one through 7 carbon atoms, cycloalkyl of 5 through 7 carbon atoms, phenyl substituted with zero through 3—R, —$OR_{50}$ or —$N(R_{50})_2$ where with the amine the $R_{50}$'s can be the same or different and can be combined to form a cyclic secondary amine selected from the group consisting of piperidine, pyrrolidine and morpholine with the proviso that $R_1$ and $R_2$ combined cannot have more than 14 carbon atoms; $R_1$ and $R_2$ can be combined to form a cyclic secondary amine selected from the group consisting of piperidine, pyrrolidine and morpholine;

$R_3$ is alkyl of one through 7 carbon atoms, cycloalkyl of 5 through 7 carbon atoms, phenyl substituted with zero through 3—R, —$OR_{50}$ or —$N(R_{50})_2$ where with the amine the $R_{50}$'s can be the same or different and can be combined to form a cyclic secondary amine selected from the group consisting of piperidine, pyrrolidine and morpholine with the proviso that $R_3$ and $R_4$ combined cannot have more than 14 carbon atoms; $R_3$ and $R_4$ can be combined to form a cyclic secondary amine selected from the group consisting of piperidine, pyrrolidine and morpholine;

$R_3'$ is alkyl of one through 7 carbon atoms, cycloalkyl of 5 through 7 carbon atoms, phenyl substituted with one through 3—R, —$OR_{50})_2$ where with the amine the $R_{50}$'s can be the same or different and can be combined to form a secondary amine selected from the group consisting of piperidine, pyrrolidine or morpholine, with the proviso that $R_3'$ and $R_4'$ combined cannot have more than 14 carbon atoms; $R_3'$ and $R_4'$ combined cannot have more than 14 carbon atoms; $R_3'$ and $R_4'$ can be combined to form a cyclic secondary amine selected from the group consisting of piperidine, pyrrolidine and morpholine;

$R_4$ is alkyl of one thru 7 carbon atoms, cycloalkyl of 5 thru 7 carbon atoms, phenyl substituted with zero thru 3—R, —$OR_{50}$ or —$N(R_{50})_2$ where with the amine the $R_{50}$'s can be the same or different and can be combined to form a cyclic secondary amine selected from the group consisting of piperidine, pyrrolidine and morpholine with the proviso that $R_3$ and $R_4$ combined cannot have more than 14 carbon atoms; $R_3$ and $R_4$ can be combined to form a cyclic secondary amine selected from the group consisting of piperidine, pyrrolidine and morpholine;

$R_4'$ is alkyl of one thru 7 carbon atoms, cycloalkyl of 5 thru 7 carbon atoms, phenyl substituted with one thru 3—R, —$OR_{50}$ or —$N(R_{50})_2$ where with the amine the $R_{50}$'s can be the same or different and can be combined to form a secondary amine selected from the group consisting of piperidine, pyrrolidine or morpholine, with the proviso that $R_3'$ and $R_4'$ combined cannot have more than 14 carbon atoms; $R_3'$ and $R_4'$ can be combined to form a cyclic secondary amine selected from the group consisting of piperidine, pyrrolidine and morpholine;

$R_6$ is a hydrogen or fluorine atom or methyl group;

$R_9$ is a chlorine, bromine or iodine atom or hydroxyl group as the tosylate, mesylate, or triflate ester;

$R_{16}$ is a hydrogen atom, hydroxyl, acyloxy where the acyl group contains 2 thru 6 carbon atoms, or methyl group with the proviso that when $R_{16}$ is a hydroxyl group and when $R_{17}$ is a hydrogen atom the hydroxyl groups at $C_{16}$ and $C_{17}$ can be in the form of an acetonide;

$R_{17}$ is a hydrogen atom or a —$COR_{17\alpha}$ group with the proviso that when $R_{17}$ is a hydrogen atom and $R_{16}$ is a hydroxyl group the hydroxyl groups at $C_{16}$ and $C_{17}$ can be in the form of an acetonide;

$R_{17\alpha}$ is an alkyl of one thru 6 carbon atoms or phenyl;

$R_{21}$ is alkyl of one thru 6 carbon atoms or phenyl, or phenyl substituted with p-nitro or m-methoxy groups;

$R_{50}$ is a hydrogen atom or alkyl of 1 thru 3 carbon atoms;

$\sim$ indicates the attached atom or group can be in the alpha or beta configuration; and ..... is a single or double bond.

2. A process according to claim 1 where the 9α-substituted-11β-hydroxy steroid (I) is selected from the group consisting of $\Delta^4$-3-keto steroids

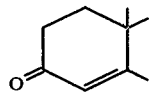

(A)

$\Delta^{1,4}$-3-keto steroids

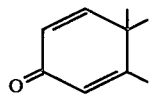

(B)

or 3β-hydroxy steroids

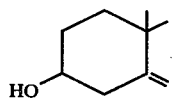

(C)

3. A process according to claim 1 where the acyclic amine is an amidine of the formula

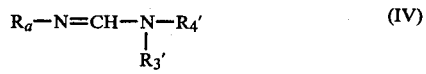

(IV)

4. A process according to claim 3 where $R_a$ is t-butyl.

5. A process according to claim 3 where $R'_3$ and $R'_4$ are both methyl groups.

6. A process according to claim 1 where the acyclic amine is a guanidine of the formula.

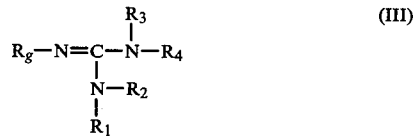

(III)

7. A process according to claim 6 where $R_g$ is a hydrogen atom.

8. A process according to claim 6 where $R_1$, $R_2$, $R_3$ and $R_4$ are all hydrogen atoms or methyl groups.

9. A process according to claim 1 where the reaction is performed in the temperature range of about 0° to about 100°.

10. A process according to claim 1 where about two equivalents of the acyclic amine per equivalent of steroid are used.

11. A process according to claim 1 where $R_9$ is a bromine atom.

12. A process according to claim 1 where the steroid D ring is

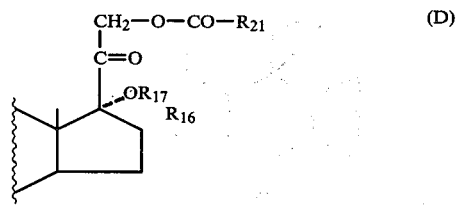

(D)

where $R_{16}$, $R_{17}$, $R_{21}$ and $\sim$ are defined in claim 1.

13. A process according to claim 1 where the 9α-substituted-11β-hydroxy steroid (I) is 9α-bromo-11β,17α,21-trihydroxypregna-1,4-diene-3,20-dione 21-acetate.

14. A process according to claim 1 where the 9α-substituted-11β-hydroxy steroid (I) is 9α-bromo-11β,17α,21-trihydroxyprena-4-ene-3,20-dione 21-acetate.

15. A process according to claim 1 where the 9α-substituted-11β-hydroxy steroid (I) is 9α-bromo-11β,17α,21-trihydroxy-16β-methylpregna-1,4-diene-3,20-dione 21-benzoate.

16. A process according to claim 1 where the 9α-substituted-11β-hydroxy steroid (I) is 9α-bromo-11β,17α,21-trihydroxy-16α-methylpregna-1,4-diene-3,20-dione 21-acetate.

17. A process according to claim 1 where the 9α-substituted-11β-hydroxy steroid (I) is 9α-bromo-6α-fluoro-11β,16α,17α,21-tetrahydroxypregna-1,4-diene-3,20-dione 16,17-acetonide-21-acetate.

18. A process according to claim 1 where the 9α-substituted-11β-hydroxy steroid (I) is 9α-bromo- 11β,16α,17α,21-tetrahydroxypregn-4-ene-3,20-dione 16,21-diacetate.

19. A process according to claim 1 where the 9α-substituted-11β-hydroxy steroid (I) is 9α-bromo-11β,16α,17α,21-tetrahydroxypregna-1,4-diene-3,20-dione 16,21-diacetate.

20. A process according to claim 6 where the acyclic amine base (III) is tetramethylguanidine.

21. A process according to claim 6 where the acyclic amine base (III) is guanidine.

22. A process according to claim 3 where the acyclic amine base (IV) is t-butyldimethylamidine.

23. A process according to claim 1 wherein the 9α-substituted-11β-hydroxy steroid (I) is 9α-bromo-11β,16α,17α,21-tetrahydroxypregn-4-en-3,20-dione 21-acetate.

24. A process according to claim 1 wherein the 9α-substituted-11β-hydroxy steroid (I) is 6α-fluoro-9α-bromo-11β,16α,17α,21-tetrahydroxypregn-4-en-3,20-dione 21-acetate.

25. A process according to claim 1 wherein the 9α-substituted-11β-hydroxy steroid (I) is 9α-bromo-11β,16α,17α,21-tetrahydroxypregna-1,4-diene-3,20-dione 21-acetate.

26. A process according to claim 1 wherein the 9α-substituted-11β-hydroxy steroid (I) is 6α-fluoro-9α-bromo-11β,16α,17α,21-tetrahydroxypregna-1,4-diene-3,20-dione 21-acetate.

27. A process according to claim 1 wherein the 9α-substituted-11β-hydroxy steroid (I) is 9α-bromo-11β,17α,21-trihydroxy-16β-methylpregna-1,4-diene-3,20-dione 17,21-diacetate.

28. A process according to claim 1 wherein the 9α-substituted-11β-hydroxy steroid (I) is 9α-bromo-11β,17α,21-trihydroxy-16β-methylpregna-1,4-diene-3,20-dione 17-benzoate.

29. A process according to claim 1 wherein the 9α-substituted-11β-hydroxy steroid (I) is 9α-bromo-11β,17α,21-trihydroxy-16β-methylpregna-1,4-diene-3,20-dione 21-pivalate.

30. A process according to claim 1 wherein the 9α-substituted-11β-hydroxy steroid (I) is 9α-bromo-11β,17α,21-trihydroxy-16β-methylpregna-1,4-diene-3,20-dione 21-valerate.

31. A process according to claim 1 wherein the 9α-substituted-11β-hydroxy steroid (I) is 9α-bromo-11β,17α,21-trihydroxy-16β-methylpregna-1,4-diene-3,20-dione 21-propionate.

32. A process according to claim 1 wherein the 9α-substituted-11β-hydroxy steroid (I) is 9α-bromo-11β,17α,21-trihydroxy-16β-methylpregna-1,4-diene-3,20-dione 17,21-dipropionate.

33. A process according to claim 1 wherein the 9α-substituted-11β-hydroxy steroid (I) is 6α-fluoro-9α-bromo-11β,17α,21-trihydroxypregna-1,4-diene-3,20-dione 17,21-diacetate.

* * * * *